US00PP11676P

United States Patent [19]

Trees

[11] Patent Number: Plant 11,676

[45] Date of Patent: Dec. 12, 2000

[54] GERANIUM PLANT NAMED 'BALDESVIO'

[75] Inventor: Scott C. Trees, Nipomo, Calif.

[73] Assignee: Ball Floraplant, a division of Ball Horticultural Co., West Chicago, Ill.

[21] Appl. No.: 09/255,313

[22] Filed: Feb. 22, 1999

[51] Int. Cl.[7] ..... A01H 5/00

[52] U.S. Cl. ..... Plt./329

[58] Field of Search ..... Plt./329, 325, 328, Plt./330

*Primary Examiner*—Howard J. Locker
*Assistant Examiner*—Wendy A Baker
*Attorney, Agent, or Firm*—C. A. Whealy

[57] ABSTRACT

A new and distinct cultivar of Geranium plant named 'Baldesvio', characterized by its numerous semi-double reddish purple-colored flowers; upright growth habit; basal branching; good vigor; and medium green leaves with faint darker green zonation pattern.

1 Drawing Sheet

BACKGROUND OF THE INVENTION

The present invention relates to a new and distinct cultivar of Geranium plant, botanically known as *Pelargonium×hortorum*, and hereinafter referred to by the cultivar name Baldesvio.

The new Geranium is a product of a planned breeding program conducted by the Inventor in Arroyo Grande, Calif. The objective of the breeding program was to develop new cultivars with freely-branching growth habit, medium green-colored foliage, uniform flowering, and interesting flower and foliage colors.

The new Geranium originated from a cross made by the Inventor of the proprietary *Pelargonium×hortorum* selection 7797-A as the male, or pollen parent, with the proprietary *Pelargonium×hortorum* selection 8410 as the female, or seed parent. The cultivar Baldesvio was discovered and selected by the Inventor as a flowering plant within the progeny of the stated cross in a controlled environment in Arroyo Grande, Calif., in January, 1996.

Asexual reproduction of the new cultivar by terminal cuttings taken at Arroyo Grand, Calif., has shown that the unique features of this new Geranium are stable and reproduced true to type in successive generations of asexual reproduction.

SUMMARY OF THE INVENTION

The following traits have been repeatedly observed and are determined to be the unique characteristics of 'Baldesvio'. These characteristics in combination distinguish 'Baldesvio' as a new and distinct cultivar:

1. Numerous semi-double reddish purple-colored flowers.
2. Upright growth habit.
3. Basal branching and vigorous.
4. Medium green leaves with faint darker green zonation pattern.

The new Geranium can be compared to the cultivar, Americana Violet, disclosed in U.S. Plant Pat. No. 8,750. However, in side-by-side comparisons conducted in Arroyo Grande, Calif., plants of the new Geranium differ from plants of the cultivar Americana Violet in the following characteristics:

1. Plants of the new Geranium are broader than plants of the cultivar Americana Violet.

2. Leaves of plants of the new Geranium have shorter and thicker petioles than plants of the cultivar Americana Violet.

3. Plants of the new Geranium have larger flowers but fewer flowers per umbel than plants of the cultivar Americana Violet.

4. Flower color of plants of the new Geranium is more purple than flower color of plants of the cultivar Americana Violet.

A detailed comparison of plants of the cultivar Baldesvio and the cultivar Americana Violet, as grown side by side, appears in Chart A at the end of the specification.

BRIEF DESCRIPTION OF THE PHOTOGRAPH

The accompanying colored photographs illustrate the overall appearance of the new cultivar, showing the colors as true as it is reasonably possible to obtain in colored reproductions of this type.

The photograph at the bottom of the sheet comprises a top perspective view of a typical plant of 'Baldesvio'.

The photograph at the top of the sheet comprises a close-up view of a typical inflorescence of 'Baldesvio'. Flower and foliage colors in the photograph may appear different from the actual colors due to light reflectance.

DETAILED BOTANICAL DESCRIPTION

The cultivar Baldesvio has not been observed under all possible environmental conditions. The phenotype may vary somewhat with variations in environment such as temperature and light intensity, without, however, any variance in genotype. The following observations, measurements and comparisons describe plants grown in 10-cm pots in Arroyo Grande, Calif., under commercial practice in a glass-covered greenhouse with day temperatures about 20° to 22° C., night temperatures about 18° to 20° C. and light levels generally about 2,500 to 3,000 footcandles.

In the following description, color references are made to The Royal Horticultural Society Colour Chart except where general terms of ordinary dictionary significance are used.

Botanical classification: *Pelargonium×hortorum* cultivar Baldesvio.

Parentage:

*Male parent*.—Proprietary *Pelargonium×hortorum* selection 7797-A.

*Female parent*.—Proprietary *Pelargonium×hortorum* selection 8410.

Propagation:

*Type cutting*.—Terminal cuttings.

*Time to initiate roots*.—About 7 days at 18° C.

*Time to develop roots*.—About 21 days at 18° C.

*Rooting habit*.—Fibrous and freely branching.

Plant description:

*General appearance*.—Upright growth habit. Appropriate for 10 and 12.5-cm containers.

*Crop time*.—Starting with a rooted cutting, about eight weeks are required to produced a finish flowering plant in 10-cm container.

*Growth and branching habit*.—Vigorous and basally branching with about two lateral branches at the base. Pinching, that is, removal of the terminal apex, is usually not required.

*Plant height* (*to top of foliage*):—About 12 to 17 cm.

*Plant width*.—About 20 to 25 cm.

*Lateral branches*.—Length: About 10 to 11 cm. Internode length: About 1 to 2 cm. Color: 146B.

*Foliage description*.—Leaves simple, generally symmetrical, abundant, opposite. Quantity of leaves per lateral branch: About 9 to 11. Length: About 4.9 to 5.6 cm. Width: About 7.5 to 8 cm. Shape: Reniform. Apex: Rounded. Base: Cordate. Margin: Crenate. Venation: Palmate. Texture: Both surfaces slightly pubescent; velvety. Color: Young and fully expanded foliage, upper surface: 137B with faint zonation pattern, 137A in color, about 2 to 3 cm wide. Young and fully expanded foliage, lower surface: 137C. Venation, upper surface: 137C. Venation, lower surface: 137D. Petiole: Length: About 5.5 to 7 cm. Diameter: About 2 to 3 mm. Color: 137C.

Flower description:

*Flower type and habit*.—Reddish purple-colored flowers. Freely and continuously flowering. Flowers arranged in generally hemispherical umbels arising from apical leaf axils. Umbels displayed above or beyond the foliage. At full flowering, usually about three to five open umbels and one or two developing umbels per plant. Flowers semi-double and round. Umbels persistent. Not fragrant.

*Flowering season*.—Year-round under greenhouse conditions. In the garden, flowering is continous from spring until fall.

*Umbels*.—Number of flowers per umbel: About 30 to 40. Diameter: About 10.5 to 13 cm. Height: About 8 to 9 cm.

*Flowers*.—Diameter: About 5.4 to 5.6 cm. Depth (height): About 1.2 cm.

*Flower buds*.—Length: About 1.3 to 2 cm. Diameter: About 7 to 9 mm. Shape: Elliptical.

*Petals*.—Quantity: About 7 to 9 petals and about 2 to 4 irregularly-shaped petaloids per flower. Arrangement: Imbricate. Length: About 2.5 to 3.1 cm. Width: About 2 to 2.6 cm. Shape: Obovate. Apex: Rounded. Base: Attenuate. Margin: Entire. Texture: Smooth. Color, fully opened flowers: Upper two petals, upper surface: 74A; venation, 71B; towards base, 43B. Upper two petals, lower surface: 74C; venation, 74B; towards base, 43C. Lower petals, upper surface: 74A; venation, 71B. Lower petals, lower surface: 74C; venation, 74B.

*Sepals*.—Quantity: About 5, not imbricate. Length: About 1.2 to 1.3 cm. Width: About 3 to 4 mm. Shape: Lanceolate. Apex: Pointed. Margin: Entire. Texture: Pilose. Color, upper and under surfaces: 146B.

*Peduncle* (*umbel stem*) .—Length: About 16 to 18 cm. Angle: Erect. Strength: Strong. Texture: Pubescent. Color: 146B.

*Pedicel* (*individual flower stem*).—Length: About 3.5 to 4.4 cm. Angle: Upright or outward. Strength: Strong. Texture: Pubescent. Color: Base, green (146A); towards flower, 183B.

*Reproductive organs*.—Androecium: Anther size: About 2 mm. Anther color: 59A. Pollen color: 170A. Gynoecium: Ovary color: Green.

Disease resistance: Resistance to pathogens common to *Pelargonium* has not been observed.

Seed development: Seed production has not been observed.

CHART A

| CHARACTERISTIC | 'BALDESVIO' | 'AMERICANA VIOLET' |
|---|---|---|
| PLANT HEIGHT (to top of foliage) | About 12 to 17 cm | About 14 to 17 cm |
| PLANT WIDTH | About 20 to 25 cm | About 19 to 20 cm |
| LEAF LENGTH | About 4.9 to 5.6 cm | About 4.4 to 5.2 cm |
| LEAF WIDTH | About 7.5 to 8 cm | About 8 to 8.5 cm |
| PETIOLE LENGTH | About 5.5 to 7 cm | About 8 to 9 cm |
| PETIOLE DIAMETER | About 2 to 3 mm | About 1.5 to 2 mm |
| UMBEL DIAMETER | About 10.5 to 13 cm | About 9.5 to 11 cm |
| NUMBER OF FLOWERS PER UMBEL | About 30 to 40 | About 100 to 110 |
| FLOWER DIAMETER | About 5.4 to 5.6 cm | About 4.5 to 5 cm |
| FLOWER DEPTH | About 1.2 cm | About 1.6 cm |
| PETAL COLOR, UPPER PETALS, UPPER SURFACE | 74A; venation, 71B; towards base, 43B | 66A; venation, 67A; towards base, 41A |
| PETAL COLOR, UPPER PETALS, LOWER SURFACE | 74C; venation, 74B; towards base, 43C | 66B; venation, 67A; towards base, 41B |
| PETAL COLOR, LOWER PETALS, UPPER SURFACE | 74A; venation, 71B | 66A; venation, 67A |
| PETAL COLOR, LOWER PETALS, LOWER SURFACE | 74C; venation, 74B | 66B; venation, 67A |
| SEPAL LENGTH | About 1.2 to 1.3 cm | About 1 to 1.1 cm |
| PEDICEL LENGTH | About 3.5 to 4.4 cm | About 2.9 to 3.5 cm |
| PEDICEL COLOR | Base, green (146A); towards flower, 183B | 143C |

It is claimed:

1. A new and distinct cultivar of Geranium plant named 'Baldesvio', as illustrated and described.

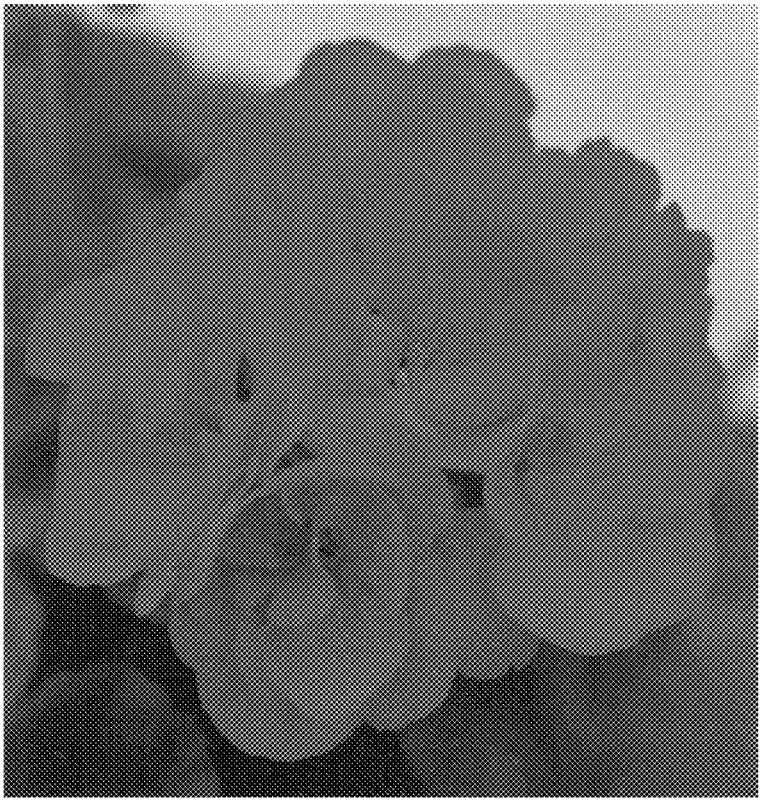
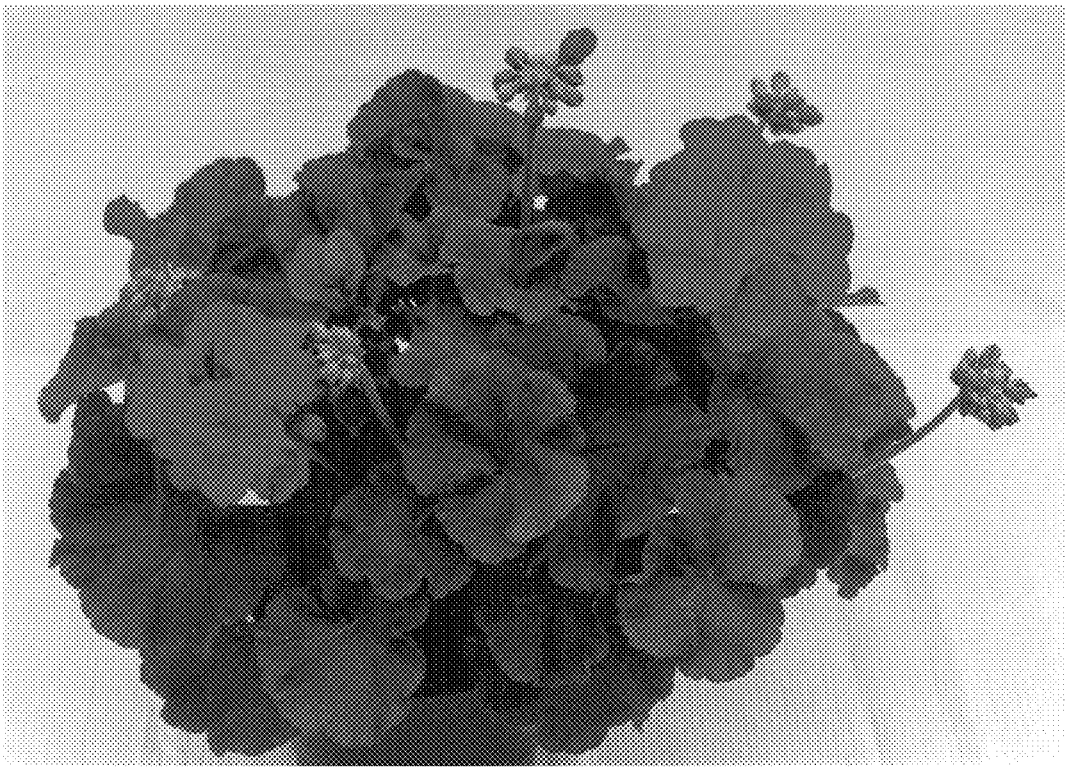

* * * * *